United States Patent [19]
Thompson et al.

[11] Patent Number: 5,167,631
[45] Date of Patent: Dec. 1, 1992

[54] PORTABLE INFUSION DEVICE

[75] Inventors: John Thompson, Rancho Santa Margarita; Giorgio di Palma, Ramona; Charles R. Botts, San Diego, all of Calif.

[73] Assignee: IMED Corporation, San Diego, Calif.

[21] Appl. No.: 761,306

[22] Filed: Sep. 17, 1991

[51] Int. Cl.⁵ .................. A61M 37/00; F01B 19/00; F16J 3/00
[52] U.S. Cl. ........................ 604/132; 92/90; 92/91; 417/437; 222/386.5
[58] Field of Search ............ 604/132, 153; 222/209, 222/212, 386.5; 417/437; 92/90, 91, 92, 96, 98 R

[56] References Cited

U.S. PATENT DOCUMENTS

| | | |
|---|---|---|
| 3,722,756 | 3/1973 | Cramer, Jr. ............... 222/386.5 X |
| 3,993,069 | 11/1976 | Buckles et al. ............... 604/132 |
| 4,968,301 | 11/1990 | di Palma et al. ............... 604/132 |
| 5,080,652 | 1/1992 | Sancoff et al. ............... 604/132 |
| 5,120,315 | 6/1992 | Hessel ............... 604/132 |

Primary Examiner—Randall L. Green
Assistant Examiner—Mary Beth O. Jones
Attorney, Agent, or Firm—Nydegger & Associates

[57] ABSTRACT

A fluid pump for infusing medical fluids to a patient includes a housing having an inlet port and an outlet port. The housing further includes a substantially hemispherically shaped surface which is circumscribed by a periphery. An elastomeric membrane is attached to the periphery of the surface and is stretched over the surface to place the membrane in its region of nonlinear elasticity. With this combination, a potential fluid chamber is established between the surface of the housing and the stretched membrane.

In operation, fluid is injected through the inlet port and into the potential chamber between the housing and the elastomeric membrane to fill the chamber with the desired medical fluid. A fluid line is connected to the outlet port of the pump and a flow restrictor is coupled with the fluid line to control the flow of fluid from the chamber. Fluid flows from the chamber as a result of the nonlinear contraction of the elastomer membrane.

24 Claims, 5 Drawing Sheets

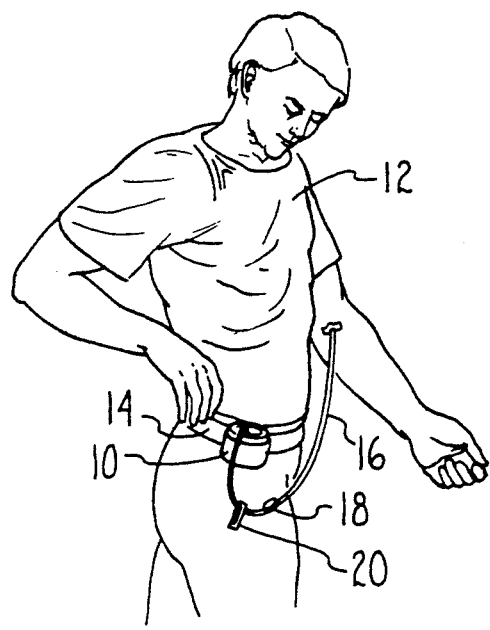
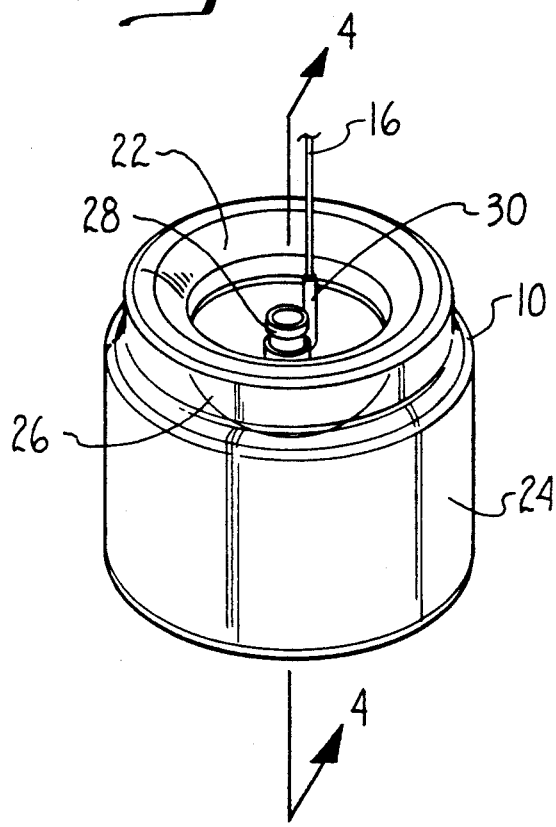
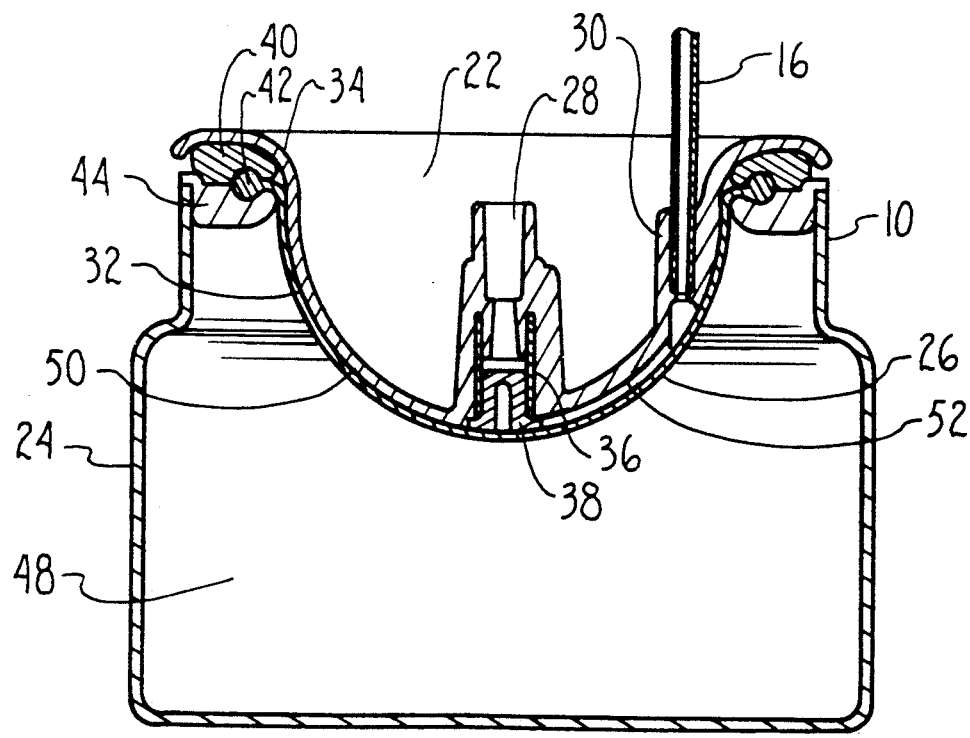

PORTABLE INFUSION DEVICE

FIELD OF THE INVENTION

The present invention pertains to fluid pumps. More particularly, the present invention pertains to portable mechanical pumps which are useful for pumping relatively small amounts of fluids under substantially constant pressure at an effectively constant rate of fluid flow over a sustained period of time. The present invention is particularly, but not exclusively, useful for a one-time use as a disposable pump for infusing fluid medicaments to an ambulatory patient.

BACKGROUND OF THE INVENTION

With recent advances in intravenous (IV) infusion pump technology, increased emphasis has been placed on establishing treatment protocols which provide a patient with earlier opportunities for greater freedom of movement. To this end, there has been a great deal of interest in the development of light weight and easy-to-use portable pumps which can be used to augment or supplement the infusion protocols which are now being accomplished using the more precise but less mobile fixed station infusion pumps. Examples of infusion pumps which are very precise and effective for their intended purposes, but which are not primarily intended for ambulatory use by a patient, include the volumetric IV pump disclosed in U.S. Pat. No. 3,985,133 which issued to Jenkins, and the peristaltic IV infusion pump disclosed in U.S. Pat. No. 4,617,014 which issued to Cannon et al., both of which are assigned to the assignee of the present invention.

For maximum flexibility in the implementation of an extended and comprehensive infusion therapy program there is a recognized need for a portable IV infusion pump or device which can be effectively used by a patient regardless whether the patient is admitted to the hospital or is in an outpatient status. Preferably, the pump can be initially set up and operated by an ambulatory patient, with little or no assistance from trained medical personnel. As a consequence, because the portable pump is most likely to be operated and used by a patient without the assistance or supervision of a medically trained attendant, the pump needs to be both reliable and accurate. This is particularly so when sophisticated medicament infusion regimens are prescribed.

To achieve the advantages of a portable ambulatory pump, several types of mechanisms have been suggested. Typically, these mechanisms are mechanical, rather than electrical. At least to some extent, this is so because electrically operated pumps require a power source and, thus, they must either include a battery or be connected to an external power source. If they require a battery, they are typically heavy or have a limited useful operating life. On the other hand, if they operate on an external power source, their range of transportability is quite limited. Further, it happens that electrical pumps are generally more complicated to use and more difficult to maintain than are purely mechanical pumps.

Of the numerous mechanical structures which have been proposed for use as a pumping chamber in portable IV infusion pumps, one structure is of particular interest. This structure is an elastomeric membrane. Indeed, an elastomeric pumping mechanism has several features which make it attractive for such an application. Firstly, an elastomeric structure is relatively inexpensive to manufacture. Secondly, it has an operational simplicity which enhances its appeal for use in devices which are to be operated by lay persons. It happens, however, that despite the simplicity of such a device not much is known or appreciated about how an elastomeric membrane works or how it can be employed with maximum efficiency.

Several examples of elastomeric pumping mechanisms for portable pumps can be cited in which various configurations for the elastomeric material are suggested. In some instances, such as for the devices disclosed in U.S. Pat. No. 4,769,008 to Hessel, and U.S. Pat. No. 4,419,096 to Leeper et al., the elastomeric membrane is tubular shaped. In other instances, such as for the device disclosed in U.S. Pat. No. 5,019,047 to Kriesel the membrane is formed as a sheet. In each case, the membrane either creates or is established as part of the fluid chamber. Consequently, subsequent to filling the chamber with fluid to stretch the membrane, the membrane is allowed to contract and thereby create fluid pressure within the chamber to pump the fluid from the chamber. Furthermore, it has been suggested that the extent of collapse of an elastomeric pumping chamber be limited. Ostensibly this is done to maintain a pressure on the fluid in the chamber at the end of the operational cycle which will cause most of the fluid to be pumped or dispensed from the chamber. This, however, does not address the problem encountered at the end of a pumping cycle which is caused by the inability of an elastomeric membrane to maintain a constant pressure within the fluid chamber as the membrane approaches its unstretched state. As is well known, constant pressure within the pumping chamber during a pumping operation is very much desired to obtain a uniform dispensing rate.

In order to maintain constant pressure on fluid during an infusion operation with a contracting elastomeric membrane, it is necessary to properly design the environment within which the elastomeric membrane will operate. This, or course, must take into account the physical capabilities of the membrane. Presently, there are no known portable infusion pumps which structurally establish the operational parameters for the collapsed state of an elastomeric pumping chamber. Consequently, portable infusion pumps that rely on the influence of a contracting elastomeric membrane to infuse fluids to a patient do not maintain the elastomeric pumping mechanism in its optimal operational mode throughout the pumping cycle. The present invention recognizes that these considerations are extremely important.

In light of the above, it is an object of the present invention to provide a portable IV infusion device which is easily transported by its user. Another object of the present invention is to provide a portable IV infusion device which is reliable and which establishes an acceptably accurate fluid infusion rate having a substantially constant flow profile. Still another object of the present invention is to provide a portable IV infusion device which provides a substantially constant pumping pressure throughout a predetermined duration for the operation of the device. Another object of the present invention is to provide an IV infusion pump which infuses fluids with substantially no residual volume in the chamber of the pump after the pumping operation has been completed. Yet another object of the present invention is to provide a portable IV infusion device which can be prefilled and stored in a ready-touse configuration for a relatively extended period of time while maintaining sterility of the fluid medicament that is held in the chamber of the device. Still another object of the present invention is to provide a disposable infusion device having a pumping chamber which can be filled to different volumes and still maintain the same fluid delivery rate regardless of the initial fill volume. Another object of the present invention is to provide a portable IV infusion pump which is easy to use, relatively simple to manufacture and comparatively cost effective.

SUMMARY OF THE INVENTION

In accordance with the present invention, a portable fluid pump includes a housing which permanently stretches an elastomeric membrane into its region of nonlinear elasticity. To do this, the housing is formed with a surface which has a predetermined contour that is circumscribed by a periphery. The elastomeric membrane is then attached to this periphery to position the membrane over and across the contoured surface of the housing. This stretches the membrane into its region of nonlinear elasticity, and create a potential fluid chamber between the surface of the housing and the elastomeric membrane. When the potential chamber is filled with fluid, the stretched membrane generates a substantially uniform fluid pressure on the fluid within the chamber for a uniform discharge of the fluid from the chamber.

For one embodiment of the portable fluid pump of the present invention, the housing is substantially hemispherical in shape and includes a fluid inlet port for introducing fluids into the potential chamber. Additionally, the housing includes a fluid outlet port for expelling fluids from the potential chamber. A fluid line is connected in fluid. communication with this outlet which acts as a flow restrictor to establish the rate of flow of fluid from the potential chamber.

As contemplated for the present invention, and as implied above, fluids are expelled from the potential chamber at a substantially constant fluid pressure by nonlinear contraction of the membrane while the membrane remains in its region of nonlinear elasticity. For purposes of the present invention, the region of nonlinear elasticity is that region wherein the generalized Hooke's law equations do not apply. Stated differently, the region of nonlinear elasticity is where the strains in the elastomeric membrane can not be expressed as a linear function of the stresses in the membrane. Preferably, the membrane is of a uniform thickness and is coated or lined with a material which is chemically compatible with fluids held in the potential chamber.

As additional structure for the portable fluid pump of the present invention, a one-way valve is mounted in cooperation with the inlet port to prevent the flow of fluid through the inlet port as fluid is pumped from the potential chamber through the outlet port. Further, the surface of the housing can be formed with an indentation which extends between the inlet port and the outlet port to vent air from the potential chamber while the chamber is being filled with fluid. As contemplated by the present invention, a fluid is loaded into the potential chamber under pressure through a valved inlet port by using another pump such as a medical syringe.

The novel features of this invention, as well as the invention itself, both as to its structure and its operation will be best understood from the accompanying drawings, taken in conjunction with the accompanying description, in which similar reference characters refer to similar parts, and in which:

BRIEF DESCRIPTION OF THE DRAWINGS

FIG. 1 is a perspective view of the portable infusion pump of the present invention shown operatively connected to a user;

FIG. 2 is a perspective view of the portable infusion pump;

FIG. 4A is a cross sectional view of the portable infusion pump as seen along the line 4—4 in FIG. 2 with the elastomeric membrane collapsed onto the housing of the portable infusion pump;

DESCRIPTION OF THE PREFERRED EMBODIMENTS

Figure 3:
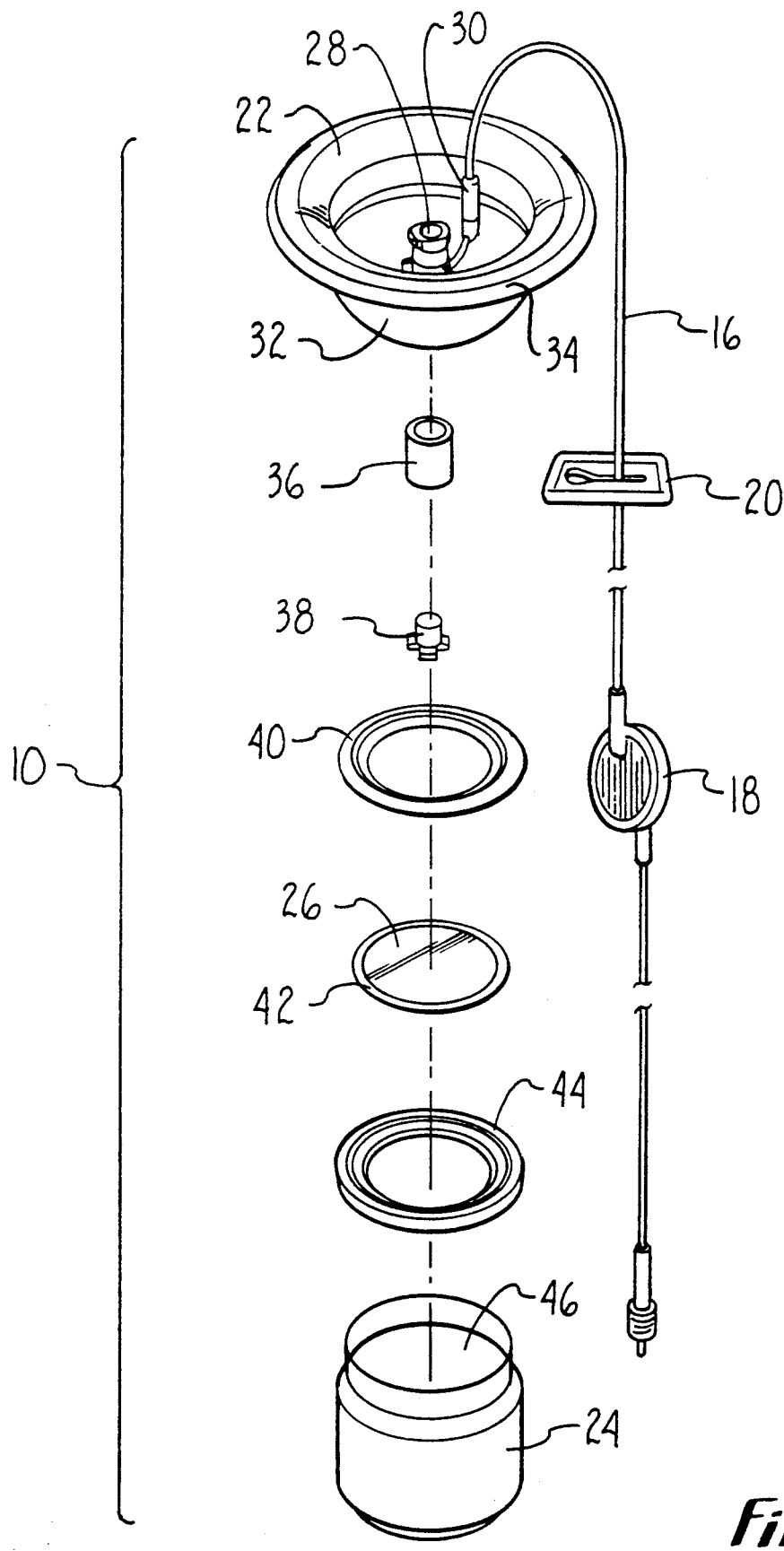
FIG. 3 is an exploded perspective view of the components of the portable infusion pump.

Referring initially to FIG. 1, a portable infusion pump in accordance with the present invention is shown and designated 10. As indicated in FIG. 1, the portable pump 10 may be worn by a user 12 during ambulation and can be attached to the user 12 by any well known means, such as a belt 14. Further, FIG. 1 shows that the portable infusion pump 10 can be connected in fluid communication with the user 12 for the infusion of fluids into the user 12 through an IV line 16. It is also shown that the IV line 16 can include an in-line air filter 18 of a type well known in the pertinent art which will prevent the infusion of air to the user 12. Additionally, a flow control 20 can be operatively associated with the IV line 16 to establish the flow of fluid from the pump 10 through the IV line 16. Although the particular flow control 20 which is shown in the Figures is a standard slide clamp, it is to be appreciated that any flow control that is well known in the pertinent art, and which has an on/off capability, will suffice for purposes of the present invention.

The combination of elemental components for the portable infusion pump 10 is, perhaps, best seen in FIG. 2 where it is shown that the pump 10 includes a housing 22 which is joined to a shell 24. An elastomeric membrane 26 is clamped between rings 40 and 44 and is then attached to the housing 22 and stretched across housing 22 between the housing 22 and the shell 24, in a manner substantially as shown. FIG. 2 also shows that the housing 22 is formed with an inlet port 28 and an outlet port 30. The individual components of portable infusion pump 10, however, are best seen in FIG. 3.

In FIG. 3 the various components of pump 10 are shown in an exploded perspective and are arranged generally in the order in which they are to be assembled. Although, the housing 22 is shown connected to the IV line 16, the housing 22 is otherwise of unitary construction. Preferably, the housing 22 is made of a hard plastic, such as polycarbonate, and is of a material which is chemically compatible with the fluid to be infused to the user 12 by the pump 10. For purposes of the present invention, the contour surface 32 of housing 22 can have any topology which will stretch the membrane 26 into its nonlinear region of elasticity when these components are assembled. Preferably, however, the contour surface 26 of housing 22 will follow and conform to the natural topology of the inflated membrane 26 as it appears in its nonlinear region. For the case shown in the Figures, contour surface 32 is substantially hemispherical. On the other hand, as shown in the Figures, the periphery 34 of housing 22 is folded outwardly from the contour surface 26 in order to facilitate the connection of the membrane 26 onto the housing 22. As will be appreciated by the skilled artisan, housing 22 can be manufactured using any well known manufacturing procedures, such as injection molding.

A thin wall table which forms valve sleeve 36, and a valve insert 38 are shown in FIG. 3 in their positions for insertion into the lumen of inlet port 28. When inserted into the lumen of inlet port 28, the sleeve 36 and valve insert 38 establish a one-way valve for the housing 22 which permits the flow of fluid in only one direction through the inlet port 28. Specifically, it is important that pump 10 be filled with fluid through the inlet port 28 but that fluid not be able to leave the pump 10 through the inlet port 28. A fluid may be loaded into the inlet port 28 under pressure utilizing a medical syringe (not shown).

The pump 10 also includes an upper top ring 40 which is engageable with a rib 42 that is located on the circumference of membrane 26. Upper ring 40 is also engageable with a lower bottom ring 44 to effectively grip and hold the rib 42 of membrane 26 between the rings 40 and 44. These rings 40 and 44 can be of any suitable rigid material such as polycarbonate which, when the rings 40 and 44 are joined together to support the flexible membrane 26, will provide a firm foundation for the membrane 26.

With specific regard to the membrane 26, it is seen in FIG. 3 that the membrane 26 is substantially a circular sheet when in its unstretched condition. Further, this sheet is formed with a raised rib 42 which, as mentioned above, can be gripped between the rings 40 and 44. Although it will be appreciated that most elastomeric materials may be suitable for the purposes of the present invention, the membrane 26 is preferably made of a natural rubber or isoprene having a high elastic memory. Regardless of the particular material used for membrane 26, however, it is important that the membrane 26 be chemically compatible with the fluid medicament which is to be infused to the user 12 from the pump 10. If there is no compatibility between the membrane 26 and the fluid medicament a drug barrier needs to be created between the two. It is known that materials such as silicone or urethane are suitable for the purpose. To establish such a drug barrier, the membrane 26 can be appropriately coated so that the particular surface of membrane 26 which is to be placed in contact with the contour surface 32 of housing 22 will not chemically interact with the fluid medicament in pump 10. Alternatively, though not shown in the Figures, a medicament compatible membrane can be held with the membrane 26 between the rings 40 and 44. With this combination, the medicament compatible membrane is positioned between the membrane 26 and the contour surface 32 of housing 22 when these components are assembled. For purposes of the present invention, the portion of membrane 26 which is circumscribed by the rib 42 is preferably of uniform thickness. It is recognized, however, that thickness may be varied across the membrane 26 as long as the resultant topology creates a nonlinear elastomeric behavior for the membrane 26.

FIG. 3 also shows that pump 10 includes a shell 24 which is basically jar shaped and which has an opening for receiving the housing 22 as it is assembled with the elastomeric membrane 26. For the preferred embodiment of the present invention, the shell 24 is made of a hard or semi-rigid plastic, such as a PETG, which can be easily manufactured by a well know process such as blow molding. Due to the possibility that variously sized membranes 26 can be used in the manufacture of a pump 10, the shell 24 can accordingly be varied in its size. More specifically, the size for shell 24 can be made compatible with the proposed maximum fluid capacity for the pump 10.

Figure 4B:
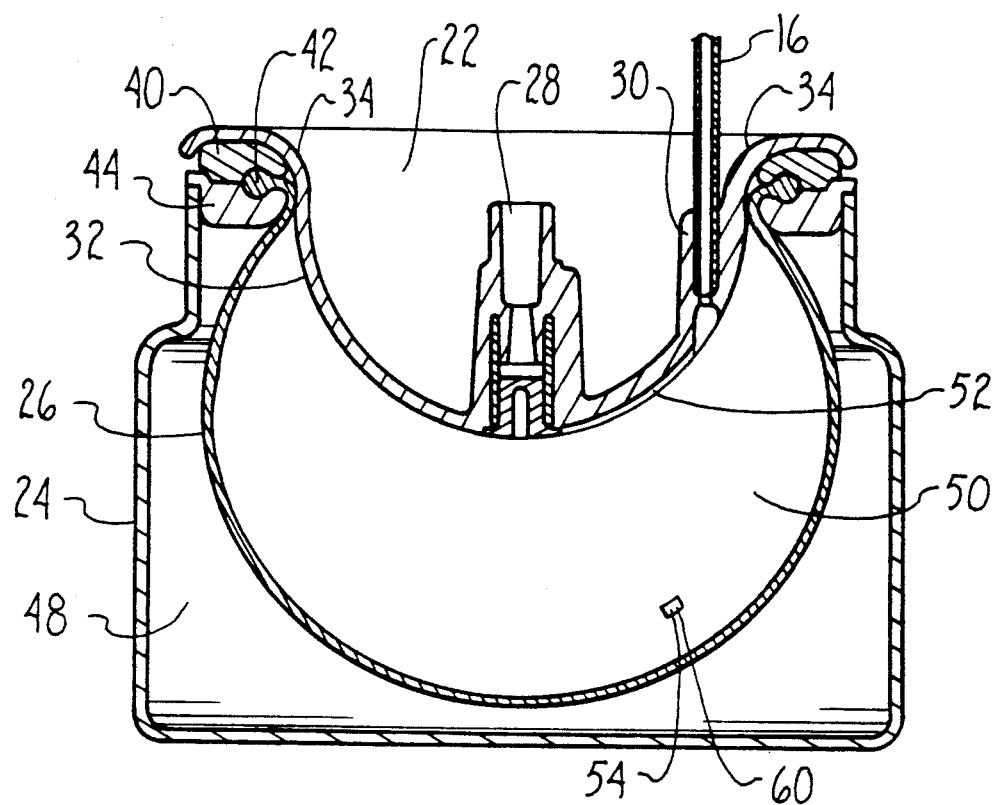
FIG. 4B is a cross sectional view of the portable infusion pump as seen in FIG. 4A with the elastomeric membrane expanded to establish a fluid chamber between the membrane and the housing of the portable infusion pump.

The cooperation of the various structural elements of pump 10 will be best appreciated with reference to both FIGS. 4A and 4B. First, in FIG. 4A it is seen that the upper top ring 40 is joined to the lower bottom ring 44 to grip and hold rib 42 of membrane 26 therebetween. The rings 40 and 44 can be joined together by any of several means, such as ultrasonic welding or solvent bonding. Lower bottom ring 44 is likewise joined to the shell 24, by the same or a similar means, to position membrane 26 across the opening 46 of shell 24 and thereby create a cavity 48 between the shell 24 and the membrane 26. Additionally, as seen in FIG. 4A, the periphery 34 of housing 22 is joined to upper top ring 40. When housing 22 is joined to upper top ring 40, the contour surface 32 of housing 22 stretches membrane 26 substantially as shown. Importantly, the dimensions of both membrane 26 and contour surface 32 are such that this stretching takes the membrane 26 into its nonlinear region of elasticity. The joining of housing 22 to upper top ring 40 also establishes a potential chamber 50 between the membrane 26 and contour surface 32.

Referring now to both FIGS. 4A and 4B, it can be appreciated that as fluid is introduced through the inlet port 28 of housing 22 and into the potential chamber 50 under the pressure of a syringe, or some other pumping means, any air in the system will first be vented to the outlet port 30 along the indentation 52 which is formed into contour surface 32. This, of course, always happens when the air pressure is less than the pressure necessary to distend the membrane 26. Then, with outlet port 30 blocked to prevent the flow of liquid medicament from chamber 50, the elastomeric membrane 26 will begin to expand as additional liquid medicament is introduced into the potential chamber 50. It is essential to the present invention that in order to create a substantially constant fluid pumping pressure in the chamber 50, the expansion, and subsequent contraction, of membrane 26 be entirely accomplished while membrane 26 is in its nonlinear region of elasticity. As previously stated the elastomeric membrane 26 is initially stretched into its nonlinear region of elasticity during assembly of the pump 10. It can be appreciated that during a subsequent loading of a fluid into chamber 50, a pump means such as a medical syringe must overcome the force which is exerted by the elastomeric membrane 26. There must then be additional non-linear stretching of the membrane 26 to form and expand the chamber 50 as shown in FIG. 4B.

Viewed from an energy standpoint, a fluid must be introduced under a pressure sufficient to overcome the potential energy of the initially stretched membrane 26. Additionally a fluid must be introduced under a pressure that is sufficient to further non-linearly stretch the membrane 26 and form the chamber 50. This total amount of energy is thus available for displacing fluid from the chamber 50. Further, because of the initial non-linear stretching of the membrane 26, even after complete discharge of a fluid, a residual force is maintained by the membrane 26 acting upon the contour surface 32.

In accordance with Hooke's law (N.B. Hooke's law does NOT apply to the operational region of membrane 26) the stress strain relationships of a nonisotropic linearly elastic material are as follows:

$$\epsilon_{xx} = C_{11}\sigma_{xx} + C_{12}\pi_{yy} + C_{13}\pi_{zz}$$

$$\epsilon_{yy} = C_{21}\sigma_{xx} + C_{22}\pi_{yy} + C_{23}\pi_{zz}$$

$$\epsilon_{xx} = C_{31}\sigma_{xx} + C_{32}\pi_{yy} + C_{33}\pi_{zz}$$

$$\epsilon_{xy} = C_{44}\sigma_{xy} \quad \epsilon_{yz} = C_{55}\sigma_{yz} \quad \epsilon_{zx} = \pi_{zx}$$

where
$\epsilon$ = tensile strain along the x, y, and z axis
$\pi$ = stress along the x, y, and z axis
C = constant Simply stated, Hooke's Law applies for the conditions wherein a change in stress is directly proportional to a change in strain. In other words, the ratio of a change in stress to a change in strain is constant (e.g. for the two dimensional case: F=kx). The present invention does not operate under these conditions.

Unlike the conditions described for Hooke's law, for the purposes of the present invention the region of nonlinear elasticity is defined as the region wherein neither elongation nor contraction of the elastomeric material obeys Hooke's law. Thus, the material does not behave as a nonisotropic linearly elastic material, and changes in stress in the material of membrane 26 are not linearly proportional to changes in the strain of the material during the operation of pump 10.

One consequence of not operating in the region of linearity where Hooke's law applies is that the response of elastomeric membrane 26 can not be modeled with elements which have a constant relationship with each other. Instead, for purposes of the present invention, a so-called four-parameter Maxwell-Voigt model is considered to be most representative of the dynamic response obtained from membrane 26 during its expansion and contraction.

Figure 5:
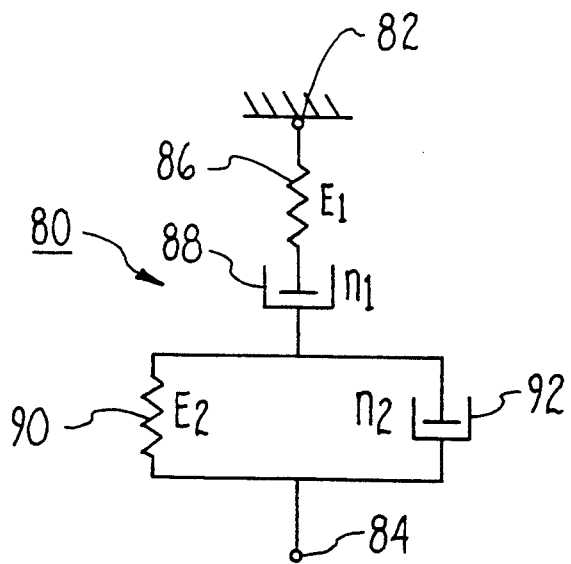
FIG. 5 is a schematic diagram of a mechanical model of a four-parameter Voigt/Maxwell elastic element.

This idealized Maxwell-Voigt model for membrane 26 is shown in FIG. 5 and is generally designated 80. As shown, model 80 includes a combination of elements which together exhibit the characteristics of instantaneous elasticity, linear creep, and retarded elasticity. In FIG. 5, this model 80 for the dynamic response of a finite element of the membrane 26 (e.g. segment 54) is shown to include a particular combination of well known mechanical elements. Specifically, these elements are shown connected together between a grounded point 82 and the point 84. For finite element analysis, the points 82 and 84 are to be considered infinitesimally close to each other. More specifically, the modeled connection between the points 82 and 84 includes the combination of a spring 86 and a dash pot 88 which are joined together in series with each other, and the combination of a spring 90 and a dash pot 92 which are joined together in parallel to each other. These two combinations of springs and dash pots are themselves joined in series between the points 82 and 84.

Using identifiable physical characteristics of the component elements of the model 80, the deformation-time curve for model 80 under a constant stress between the points 82 and 84 can be described by the rheological equation:

$$\epsilon = \frac{\sigma_o}{E_1} + \frac{\sigma_o}{E_2}(1 - \exp(t/\tau_2)) + \frac{\sigma_o}{\eta_1} t$$

Where:
E = a material constant (i.e. the modulus)
$\epsilon$ = tensile strain
$\sigma_o$ = initial stress
t = time
$\eta$ = viscosity coefficient $$\tau_2 = \frac{\eta_2}{E_2}$$

The model 80, as shown in FIG. 5, together with its corresponding deformation-time described by the equation above, are taken to represent the response of membrane 26 in its region of nonlinear elasticity. With this in mind, the physical responses of membrane 26 in its region of nonlinear elasticity will perhaps be best appreciated by analysis of a finite element.

Figure 6A:
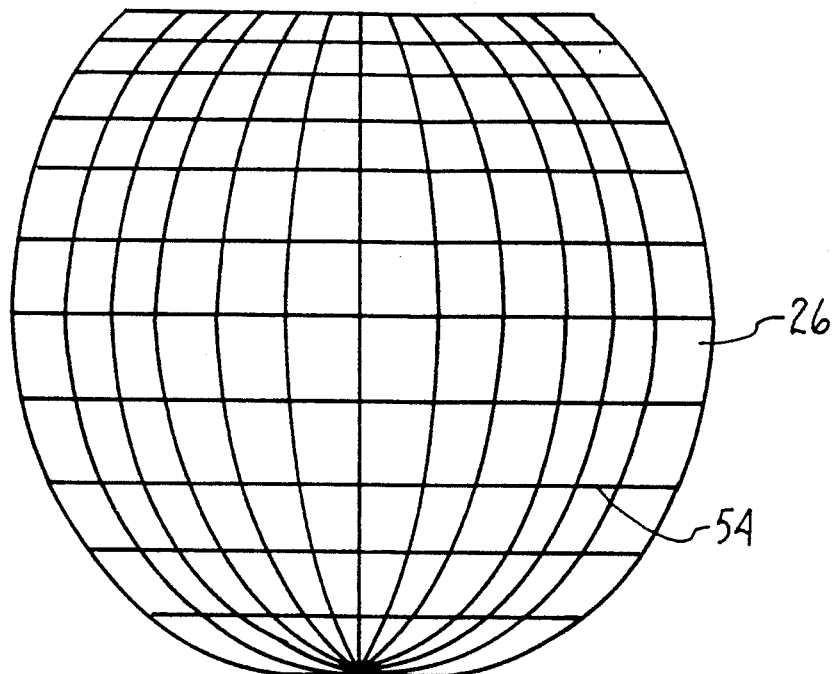
FIG. 6A is a side elevation view of the elastomeric membrane of the present invention in an expanded state with finite elements indicated on the surface of the membrane.

To begin this analysis, consider a finite element of membrane 26 such as the segment 54 shown in FIG. 4B and a more idealized illustration of the segment 54 as shown in FIG. 6A. Specifically, FIG. 6A shows membrane 26 stretched into a configuration with various finite elements (all similar to the segment 54) which have been identified on its surface. In accordance with the expansion and contraction of membrane 26, each finite element (e.g. segment 54) adjusts its dimensions and its orientation with adjacent finite elements to balance its force and its relationship with all other finite elements in the membrane 26. Thus, the ratio of force to area (i.e. pressure) generated by each finite element is equal to that of all other finite elements. This implies uniform pressure.

Figure 6B:
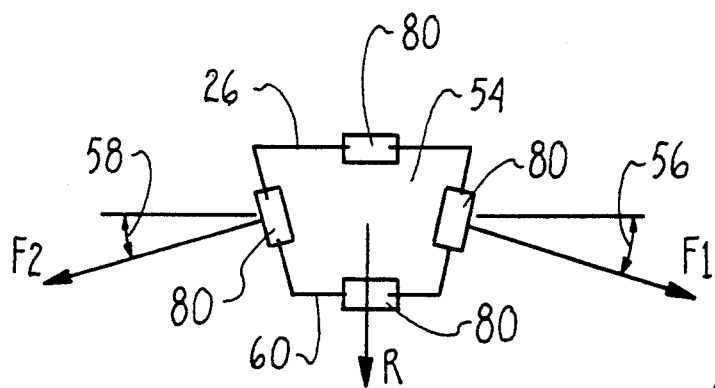
FIG. 6B is a free body diagram of a segment of an elastomeric material in a stretched condition.
Figure 6C:
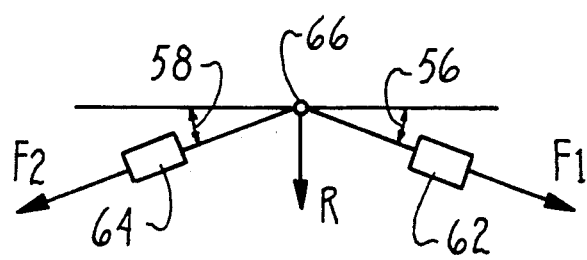
FIG. 6C is a two-dimensioned analog of the free body diagram shown in FIG. 6B.

FIG. 6B is a representative free body diagram of the segment 54 showing forces acting on the segment 54 in only two dimensions. More specifically, the forces shown acting on segment 54 in FIG. 6A are representative of a condition wherein the membrane 26 is stretched into a curved configuration. As shown, the forces in each segment 54 can be modeled using an arrangement of Maxwell-Voigt models 80 substantially as illustrated. For example, such a condition is shown for the membrane 26 in both FIG. 4A and FIG. 4B. The consequence is that the elastomeric stress forces generated in the membrane 26 ($F_1$ and $F_2$), which are shown acting on the segment 54, are not collinear, i.e. the angles 56 and 58 are not equal to zero. Thus, a resultant force R is generated that reacts with the fluid which is held within potential chamber 50.

A two dimensional simplified model of this force system, which may help in visualizing the action of membrane 26, would include a pair of Maxwell-Voigt models 62 and 64 which act together at a point 66. As shown in FIG. 6B, the Maxwell-Voigt models 62 and 64 in this arrangement will act together at point 66 to move the point 66 in the direction of the resultant force R. In accordance with vector analysis, the magnitude of this resultant force R will depend on the magnitude of the forces generated by the models 64 and 62, as well as the directions in which these forces act on the point 66. These directions are indicated in FIGS. 6A and 6B by the angles 56 and 58. The model is given here only for the purpose of visualizing that the forces which act on segment 54 are variable. For a linear analysis of this consideration consider replacing the models 62 and 64 with springs.

The achievement of a constant flow profile for portable infusion pump 10, however, is not dependent on maintaining a constant resultant force R under the elastomeric action of membrane 26. Instead, this objective is accomplished by using the membrane 26 to maintain a constant pressure on the fluid in potential chamber 50. This means it is important that the ratio of the resultant force R and the surface area 60 of segment 54 be held as nearly constant as possible during the contraction of membrane 26.

It happens that as membrane 26 contracts during a pumping operation, from a configuration as shown in FIG. 4B toward a configuration as shown in FIG. 4A, several changes occur simultaneously. Together, these changes affect the pressure which is exerted by membrane 26 on the fluid in potential chamber 50. Most significantly, as membrane 26 contracts in its region of nonlinear elasticity, the magnitude of the elastomeric forces $F_1$ and $F_2$ will decrease, the size of surface area 60 will also decrease, and the angles 56 and 58 will increase. Obviously, in order for the pressure on fluid in chamber 50 to remain constant, these variables need to be balanced. As recognized by the present invention, these variables are effectively balanced to create a substantially constant pressure in the chamber 50 so long as the membrane 26 is confined to operation in its region of nonlinear elasticity.

Figure 7:
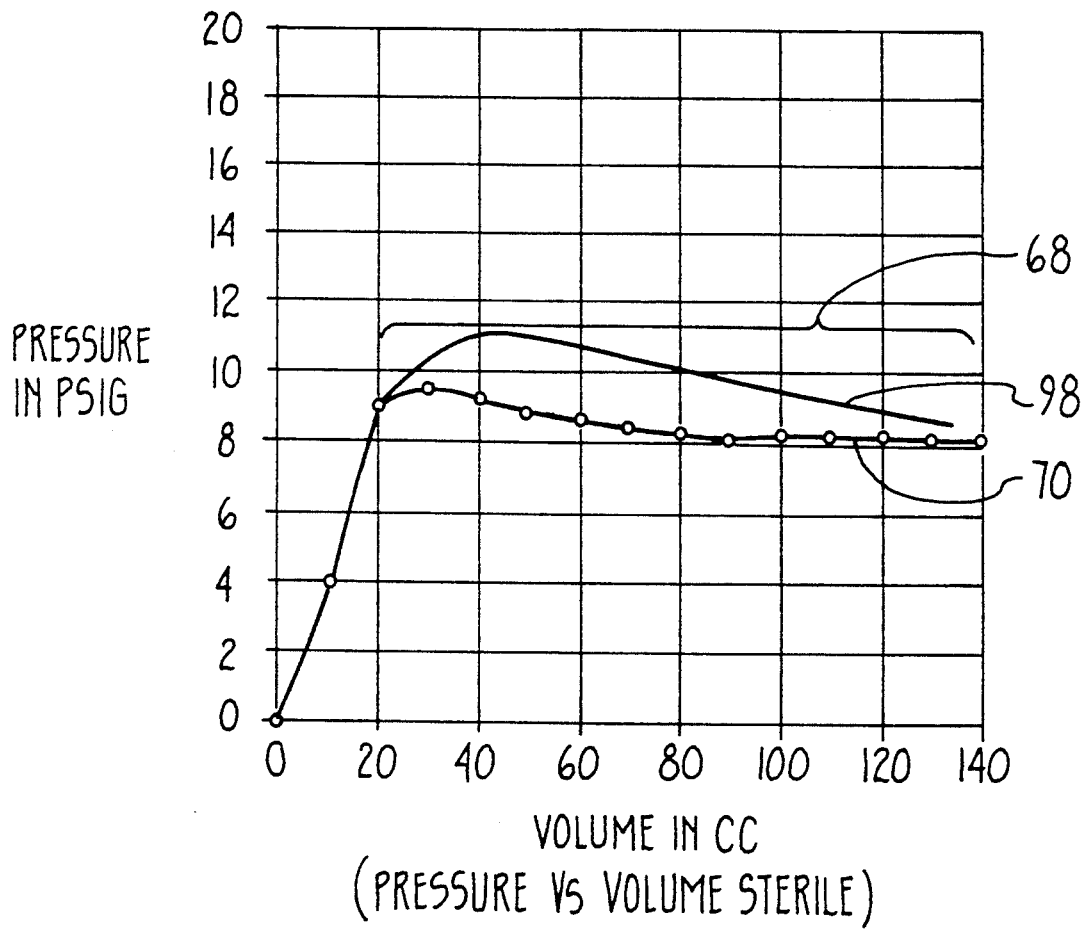
FIG. 7 is a modeled and empirically obtained Pressure Vs Volume curve for the nonlinear behavior of an elastomeric material shown in comparison with a modeled curve for the theoretical linear behavior of the material.

In FIG. 7 a region 68 of substantially constant pressure is shown to exist in FIG. 7 when the volume contained by a stretched elastomeric membrane such as membrane 26 is greater than approximately twenty cubic centimeters (20 cc). Specifically, the curve 70 shown in FIG. 7 represents an empirical plot of the pressure which is exerted on a fluid body by an initially flat circular elastomeric membrane 26 which has a predetermined thickness and a predetermined diameter. More specifically, the curve 70 is generated as the membrane 26 is constrained at its periphery and is expanded from its unstretched or relaxed condition. Curve 70 also represents the variation in pressure which will be exerted by the membrane 26 as it contracts and collapses toward its unstretched or relaxed condition. For purposes of the present invention the effect of hysteresis is negligible. As will be appreciated, the physical dimensions of membrane 26 can be varied with some consequent variations in the curve which is generated. For purposes of discussion, however, the curve 70 of FIG. 7 is considered to be representative of a typical response for membrane 26.

An important factor is illustrated in FIG. 7, which establishes a significant structural design criteria for the pump 10. For a particular membrane 26, this factor is that the region 68 of curve 70, wherein a substantially constant pressure can be exerted by membrane 26 on fluid in chamber 50, occurs only after the membrane 26 has been initially stretched to contain a volume that is equal to approximately twenty cubic centimeters. This contained volume thus establishes a boundary condition for the displacement volume which needs to be created by contour surface 32 of housing 22. Curve 70, as earlier indicated, is derived empirically and verified by modeling for the nonlinear response of membrane 26. In contrast to the curve 70, the curve 98 is the result of modeling for a linear response. Importantly, in the region 68, curve 70 is flatter and thus indicates a more constant pressure. Also it is to be noted that, for the particular membrane 26, the deviation of curve 70 occurs at approximately twenty-five cubic centimeters (25 cc) for the particular elastomeric which was modeled and tested.

As recognized by the present invention, the boundary conditions which are necessary to insure only nonlinear operation for any given membrane 26 will vary according to several factors. Importantly, these factors include the stress-strain properties of the material which is used for the manufacture of membrane 26 and the initial displacement volume of contour surface 32. For the membrane 26, additional factors include the geometry of membrane 26, i.e. its diameter, and its thickness. All of these variables need to be engineered so that once membrane 26 is positioned across contour surface 32, all of membrane 26 that is in contact with contour surface 32 will be stretched into its region of nonlinear elasticity. With this in mind, it can be appreciated that a curve 70 corresponding to other geometries for membrane 26 can be generated and that the region 68 will vary accordingly. Consequently, the initial volume required to be spaced or displaced by surface 32 will also vary. Ideally, the volume displaced by surface 32 will be approximately equal to the measured volume where the linear and non-linear response separate.

An understanding of the pumping action which is established by the elastomeric contraction of a membrane 26 is but one, albeit extremely important, facet of the operation of pump 10. Equally important is an understanding of the resultant fluid dynamics in the system. With regard to the fluid dynamics, it is known that the laminer flow of a fluid medicament from the pump 10 to the user 12 will comply with the following general equation:

$$P_{device} - P_{patient} = flowrate * restrictor\ resistance$$

From this general equation (which is essentially a restatement of the Hagen-Poiseuille equation) it can be appreciated that to obtain a substantially constant flowrate, the pressure generated by the pump 10 ($P_{device}$) must be effectively constant. This, also assumes that the pressure generated by the patient ($P_{patient}$) is also effectively constant. Fortunately, under the conditions of laminar flow operation for the present invention, this assumption is acceptable. Therefore, it will follow that the flow of fluid through IV line 16 can be characterized by the Hagen-Poiseuille equation. This equation is:

$$V = \frac{\Delta p \pi D^4}{128 \mu L}$$

where:
V = velocity of fluid flow;
r = radius of the flow restrictor conduit;
Δp = energy loss (i.e. pressure change over a length L);
L = length of flow restrictor; and
μ = fluid viscosity.

According to the Hagen-Poiseuille equation, if there is a constant energy loss over the length of a tube, then a constant flowrate of fluid through the tube can be established by properly designing the physical characteristics of the tube.

Theoretically, it can be accepted that with $P_{device}$ substantially constant, there will be an effectively constant energy loss along the IV line 16. This is so because, as indicated above, we are assuming that $P_{patient}$ is effectively constant and that the boundary conditions for operation of the membrane 26 are properly established so that $P_{device}$ is also effectively constant. Accordingly, there will be a constant flowrate through IV line 16, when the conditions are such that $P_{device} - P_{patient}$ is constant. As a practical matter, $P_{patient}$ is negligibly small. Therefore, the non pulsitile linear flow of pump 10 is due almost entirely to the constant pressure engineered for pump 10.

The result is that in order to establish a specific value for the flowrate of fluid from pump 10 through IV line 16 to user 12, both $P_{device}$ and the physical design of IV line 16 must each be engineered with consideration for the other. The considerations which attend the design of $P_{device}$ have been discussed above. At this point it is sufficient to recognize that the design of IV line 16 will depend specifically on the radius of the lumen in IV line 16 and the length of the IV line 16.

While the particular portable IV infusion pump as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. A device for pumping fluids which comprises:
    a housing having a first fluid port, said housing being formed with a surface having a periphery and a predetermined contour circumscribed by said periphery; and
    an elastomeric membrane attached to said periphery over said contour surface to stretch said membrane into a nonlinear region of elasticity and create a potential chamber between said stretched membrane and said housing for receiving fluid therein through said first port and expelling fluid therefrom through a second port by nonlinear contraction of said membrane at a substantially constant pressure.

2. A device as recited in claim 1 wherein said membrane is of a uniform thickness.

3. A device as recited in claim 1 wherein said predetermined contour is substantially hemispherical in shape.

4. A device as recited in claim 1 wherein said membrane is coated to be chemically compatible with fluids injected through said port into said potential chamber.

5. A device as recited in claim 1 wherein said first port is an inlet port for filling said potential chamber and said second port comprises an outlet port for expelling fluid from said potential chamber.

6. A device as recited in claim 5 further comprising a one-way valve mounted in said inlet port to prevent the flow of fluid from said potential chamber through said inlet port.

7. A device as recited in claim 5 further comprising an indentation formed in said surface of said housing between said inlet port and said outlet port for venting air from said potential chamber while said chamber is being filled with fluid.

8. A device as recited in claim 1 further comprising a shell attached to said periphery of said housing to position said membrane between said housing and said shell to protect said potential chamber.

9. A fluid pump which comprises:
    an elastomeric membrane;
    means for stretching said membrane into its region of nonlinear elasticity;
    means for mounting said membrane on said stretching means to create a potential fluid chamber therebetween; and
    means for expelling fluid from said potential chamber said means for expelling comprising the nonlinear contraction of said membrane while said membrane remains in said region of nonlinear elasticity.

10. A fluid pump as recited in claim 9 wherein said stretching means is a housing formed with a surface having a periphery and a predetermined contour circumscribed by said periphery and wherein said elastomeric membrane is attached to said periphery over said contour.

11. A fluid pump as recited in claim 10 wherein said expelling means is an outlet port formed on said housing and said housing further includes an inlet port for introducing fluids into said potential chamber.

12. A fluid pump as recited in claim 11 further comprising a one-way valve mounted in said inlet port to prevent the flow of fluid from said potential chamber through said inlet port and said pump further comprises an indentation formed in said surface of said housing between said inlet port and said outlet port for venting air from said potential chamber while said chamber is being filled with fluid.

13. A fluid pump as recited in claim 9 wherein said predetermined contour is substantially hemispherical in shape.

14. A fluid pump as recited in claim 9 wherein said membrane is of a uniform thickness and is coated to be chemically compatible with fluids in said potential chamber.

15. A fluid pump as recited in claim 12 further comprising a fluid line connected in fluid communication with said outlet and a flow restrictor coupled with said fluid line for controlling the flow of fluid from said potential chamber through said fluid line.

16. A method for using fluid medicaments to a patient which comprises the steps of:
    providing a fluid pump comprising a housing having a fluid port, said housing being formed with a surface having a periphery and a predetermined contour circumscribed by said periphery;

an elastomeric membrane attached to said periphery over said contour to stretch said membrane into a nonlinear region of elasticity and create a potential chamber between said stretched membrane and said housing for receiving fluid therein through said port and expelling fluid therefrom through said port by nonlinear contraction of said membrane;

filling said potential chamber through said port;

connecting said port in fluid communication with the patient; and expelling fluid from said potential chamber to the patient through said port by nonlinear contraction of said membrane while said membrane remains in said nonlinear region of elasticity.

17. A method as recited in claim 16 wherein said port comprises an inlet port for filling said potential chamber and said port further comprises an outlet port for expelling fluid from said potential chamber.

18. A method as recited in claim 16 wherein said membrane is of a uniform thickness and said predetermined contour is substantially hemispherical in shape.

19. A method as recited in claim 16 wherein said pump further comprises a fluid line connected in fluid communication with said outlet and a flow restrictor coupled with said fluid line for controlling the flow of fluid from said potential chamber through said fluid line and said method further comprises the step of manipulating said flow restrictor to control the flow of fluid from said potential chamber through said fluid line.

20. A fluid pump comprising:

a housing including a contoured surface;

an elastomeric membrane mounted on the housing and stretched over the contoured surface into a region of non-linear elasticity during assembly of the pump;

inlet means for introducing a fluid under pressure between the elastomeric membrane and contoured surface to further non-linearly stretch the membrane, and form a chamber therebetween; and outlet means for discharging a fluid from the chamber under a pressure exerted by the elastomeric membrane;

whereby a substantially uniform fluid pressure is exerted by the non-linearly stretched membrane upon the fluid during contraction of said membrane and a residual pressure is exerted by the membrane upon the contour surface after total discharge of the fluid.

21. A fluid pump as recited in claim 20 wherein the inlet means includes a one way valve adapted to receive fluid from a medical syringe.

22. A fluid pump as recited in claim 20 wherein the contour surface is formed with an indentation for venting air into the outlet means.

23. A fluid pump as recited in claim 20 wherein the membrane is stretched to form a chamber that contains a volume substantially equal to a volume necessary to maintain said membrane in said region of nonlinear elasticity.

24. A fluid pump as recited in claim 23 and wherein the membrane is formed of a material, diameter and thickness to exert a pressure of about 6 psig.

* * * * *

Adverse Decisions In Interference

Patent No. 5,167,631, John Thompson, Giorgio Di Palma, Charles R. Botts, PORTABLE INFUSION DEVICE, Interference No. 103,347, final judgment adverse to the patentees rendered March 25, 1999, as to claims 1 and 20.

*(Official Gazette May 2, 2000)*